United States Patent
Bors et al.

[11] Patent Number: 5,535,616
[45] Date of Patent: Jul. 16, 1996

[54] APPARATUS AND METHOD FOR THE ANALYSIS OF POROUS MATERIALS

[75] Inventors: Hans Bors, Fällanden; Walter Lüthi, Ebnat-Kappel, both of Switzerland

[73] Assignee: Hans Bors Habotex-Consulting, Fallanden, Switzerland

[21] Appl. No.: 291,607

[22] Filed: Aug. 16, 1994

[30] Foreign Application Priority Data

Aug. 31, 1993 [CH] Switzerland ............... 02587/93

[51] Int. Cl.$^6$ ............................................. G01N 15/08
[52] U.S. Cl. ................................................... 73/38
[58] Field of Search ........................... 73/38, 64.47, 78

[56] References Cited

U.S. PATENT DOCUMENTS

| | | | |
|---|---|---|---|
| 2,755,660 | 7/1956 | Kammermeyer et al. | 73/38 |
| 3,248,930 | 5/1966 | Speegle et al. | 73/38 |
| 3,577,767 | 5/1971 | Stedile | 73/38 |
| 3,590,634 | 7/1971 | Pasternak et al. | 73/38 |
| 3,604,246 | 9/1971 | Toren | 73/38 |
| 4,385,517 | 5/1983 | Sorce et al. | 73/38 |
| 4,468,951 | 9/1984 | Garcia et al. | 73/38 |
| 4,846,970 | 7/1989 | Bertelsen et al. | 73/38 |
| 5,382,894 | 1/1995 | Beckstein et al. | 324/71.1 |

FOREIGN PATENT DOCUMENTS

| | | |
|---|---|---|
| 0148290 | 7/1985 | European Pat. Off. . |
| 0529455 | 3/1993 | European Pat. Off. . |
| 3638483 | 5/1987 | Germany . |
| 161532 | 10/1982 | Japan ................ 73/64.47 |
| 282633 | 11/1988 | Japan ................ 73/38 |
| 643787 | 1/1979 | U.S.S.R. ............. 73/38 |
| WO9010211 | 9/1990 | WIPO . |

OTHER PUBLICATIONS

J. A. Jonsson et al., "Supporeted liquid membrane techniques for sample preparation and enrichment in environmental and biological analysis", TrAC: Trends in Analytical Chemistry, vol. 11, No. 3, (Mar. 11, 1991).

*Primary Examiner*—Hezron E. Williams
*Assistant Examiner*—Daniel S. Larkin
*Attorney, Agent, or Firm*—Marks & Murase

[57] ABSTRACT

An apparatus for the determination of the inner condition of a porous material, particularly a textile material web, and a method for running the apparatus. The apparatus comprises a pressure element and an extracting and collecting element which clamp the material between them; the clamped-in sample is then extracted with a preferably hot extracting fluid. The extract will then be analyzed in order to yield indications of the inner condition of the material and/or of substances present in or on the porous material.

22 Claims, 5 Drawing Sheets

APPARATUS AND METHOD FOR THE ANALYSIS OF POROUS MATERIALS

The present invention refers to a device or apparatus for the analysis of porous materials which contain extractable substances, in order to determine the inner condition of the material, such as substances present in or on the material, by forced desorption and extraction. More particularly, this invention is directed to the analysis of textile materials, especially of such materials in sheet or web form, but also in the form of parallel strands of filaments, by means of water, aqueous liquids, or organic solvents.

BACKGROUND OF THE INVENTION

In the manufacturing-industries, there is often the necessity of determining the inner condition of a porous material, particularly in sheet or web form, referring to substances which are enclosed within its interior where a simple or direct access is not possible. This applies for example to the textile industry, particularly to the finishing steps where finishing agents are applied to the textile material and are absorbed by the latter. For finishing, such as dyeing, sizing, high-grade finishing, fast finish, crease resist finish, hydrophobing, mercerizing etc., a treating liquor or a gas mixture is generally applied in excess, the excess is removed after impregnation, and the textile material is further processed, for example in a reaction step, by condensing, drying, washing, applying further finishing agents, etc.

In all cases, modern economical and ecological necessities require the application of the minimum amount of treating agents. This, in turn, requires the knowledge of the amount of free, unused substances which have remained in the textile material after the finishing and reaction steps. Only if these values are known, can the preceding treatment steps be optimized as to the amount of treating agents really required. The determination of these values should be rapid and should not destroy the material to be assayed.

In this sense, the expression "analysis" as used herein means the determination of the condition within materials as defined above but also, more generally, the determination of substances contained in or on porous materials.

It is generally well known to cut samples from porous web materials and to extract substances in excess from these samples. However, these techniques partially destroy the material and make relatively large portions thereof unusable.

As to non-destructive analysis methods, European patent application No. EP-A2-0,529,455 discloses a method and a device for the continuous measurement of the presence of ionic and nonionic substances in a running textile material web. For example, a solvent is sprayed or otherwise applied from one side onto a definite region of the running web, and the solvent or the solution draining through the textile material is collected from the other side of the web. This method and device only supplies rough values since there are no definite conditions: part of the solvent necessarily remains in the web by absorption. The solvent is applied by a moving device, and there is no certainty whether the amount of solvent used throughout the application surface is uniform or not. Generally, relatively huge amounts of extracting solvents must be used which yield only very diluted extracts. Furthermore, the method cannot be used on dry textile material.

The first and major object of the present invention is to provide an apparatus which allows the exact and rapid extraction of flat, porous materials, particularly textile materials, so that the inner condition of the materials can rapidly and exactly be determined.

Another object of the invention is to provide a method as depicted above which, during extraction of the porous material, creates certain conditions and states which are reproducibly defined and which, on the other hand, allow a complete, quantitative desorption of extractible substances from the porous substrate to be assayed.

Still another object of the present invention is to provide a method of extraction and collection of the extracted fluids by means of the apparatus according to this invention, which yields liquid samples quantitatively representing the inner condition of the substrate that can easily and rapidly be assayed by using only small volumes of extracting fluid.

SUMMARY OF THE INVENTION

Now, to implement the objects listed above and still others, the apparatus of the present invention comprises a pressure element and a collecting element both having a central axis, said axes being aligned with each other, said elements being fastened to a support system comprising two parallel support beams, and the apparatus further comprises means for pressing the two said elements together in clamping the said porous material between them, and means for supplying extraction liquid and for recovering and collecting the extract from the porous material.

Preferred embodiments of the apparatus will be described later on as well as the method of the invention.

The apparatus of the invention may be used in principle with any porous materials whatsoever having open pores which allow the passage of fluids and in which substances are enclosed which can be taken up by the said fluid which is the extraction medium and be carried out of the materials; two-dimensional, i.e. sheet or web like materials being preferred. The extraction fluid may very easily be adapted to the nature, particularly the solubility, of the substances expected within the porous materials. Generally, water is used, for example deionized water, which will be heated in the apparatus of the invention to about 70° to 100° C., preferably to about 90° to 95° C. Aqueous solutions may also be used; an example is the use of diluted alkali for the extraction of acids without losses and with more ease. Examples of other extraction fluids which may be used are condensing steam, mixtures of steam and water, mixtures of air or other gases with water, mixtures of water and carbon dioxide, mixtures of water with organic liquids which need not be soluble in water such as alcohols, ketones, amides, ethers, esters, acids, bases, all these liquids being optionally mixed with steam or other vapours and gases, emulsions of water with water insoluble or partially soluble liquids, dimethyl sulfoxide, dimethyl formamide and non-aqueous liquids such as methanol, ethanol, acetone, dioxane, etc. This listing is by no means exhaustive. The extracting fluid may further contain additives such as surface active agents. It is also possible to use selectively acting extraction fluids; for example, if water soluble acids should be determined besides other water insoluble substances, an aqueous base will be used as an extraction fluid which preferably extracts the acids. Although it is preferred to use warm or hot extraction fluids, sometimes even superheated ones, the apparatus of the invention allows also cold extraction processes.

The porous materials to be extracted may be those already mentioned above. Textile materials are particularly important, such as webs or clothes of woven fabrics, woven knittings, non-wovens, pole fabrics, etc. The invention allows an analysis of enclosed substances without destruction or damage of the material and is particularly suited for use in test and industrial laboratories since only small volumes of extraction fluid are used and the analysis may be executed very rapidly.

The apparatus and the method of the present invention will now be explained in more detail by means of the drawing and the description of an embodiment of the apparatus; however, it is to be noted that the invention is not limited to this example.

DETAILED DESCRIPTION OF THE INVENTION

Figure 1:
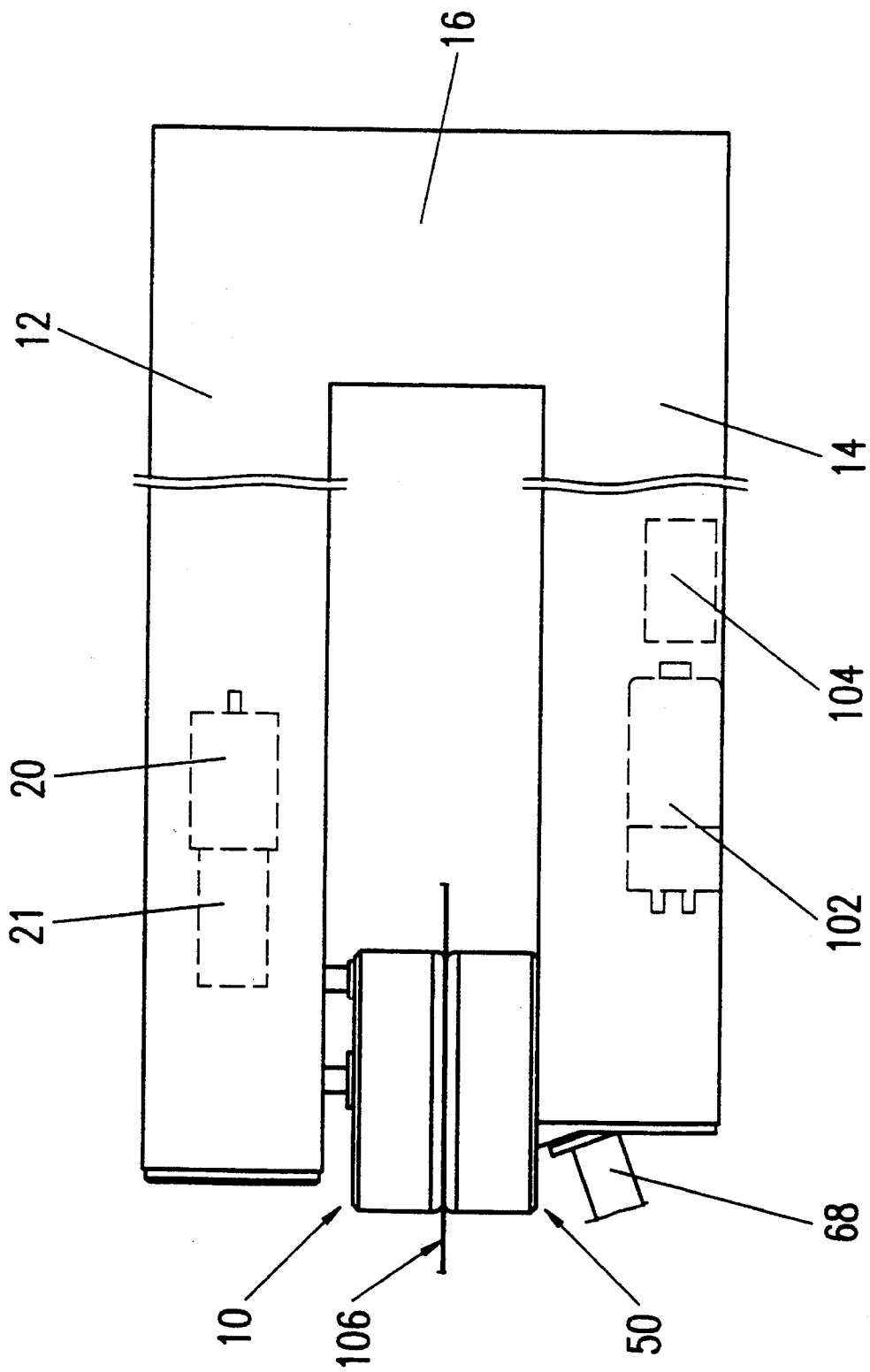
FIG. 1 shows schematically a general side view of the apparatus to be described.

The apparatus which is schematically shown in FIG. 1 comprises two main parts, namely the sampling device comprising the appertaining driving parts, and a control and display device (not shown) which contains the necessary control devices and display elements; all these devices and elements (not shown, but familiar to the one skilled in the art) are mounted in a control cabinet which is not shown either.

The sampling device comprises two major parts, namely the pressure element 10, also called upper shoe, and the extracting and collecting element or lower shoe 50; these elements will be described in detail later. Both elements are disposed at the front end of support bars 12 and 14, respectively, which are rigidly connected to each other at their rear ends by a traverse 16, e.g. by welding. The support bars 12 and 14 are hollow profiles in the shown embodiment and can therefore contain other elements of the apparatus. The free length of the support bars 12 and 14 is selected such that they are adapted to the width of a web 106 of a porous sheet material to be analyzed, generally a textile material, see below. As it is further shown in FIG. 1, the material 106 is clamped between elements 10 and 50.

Figure 2:
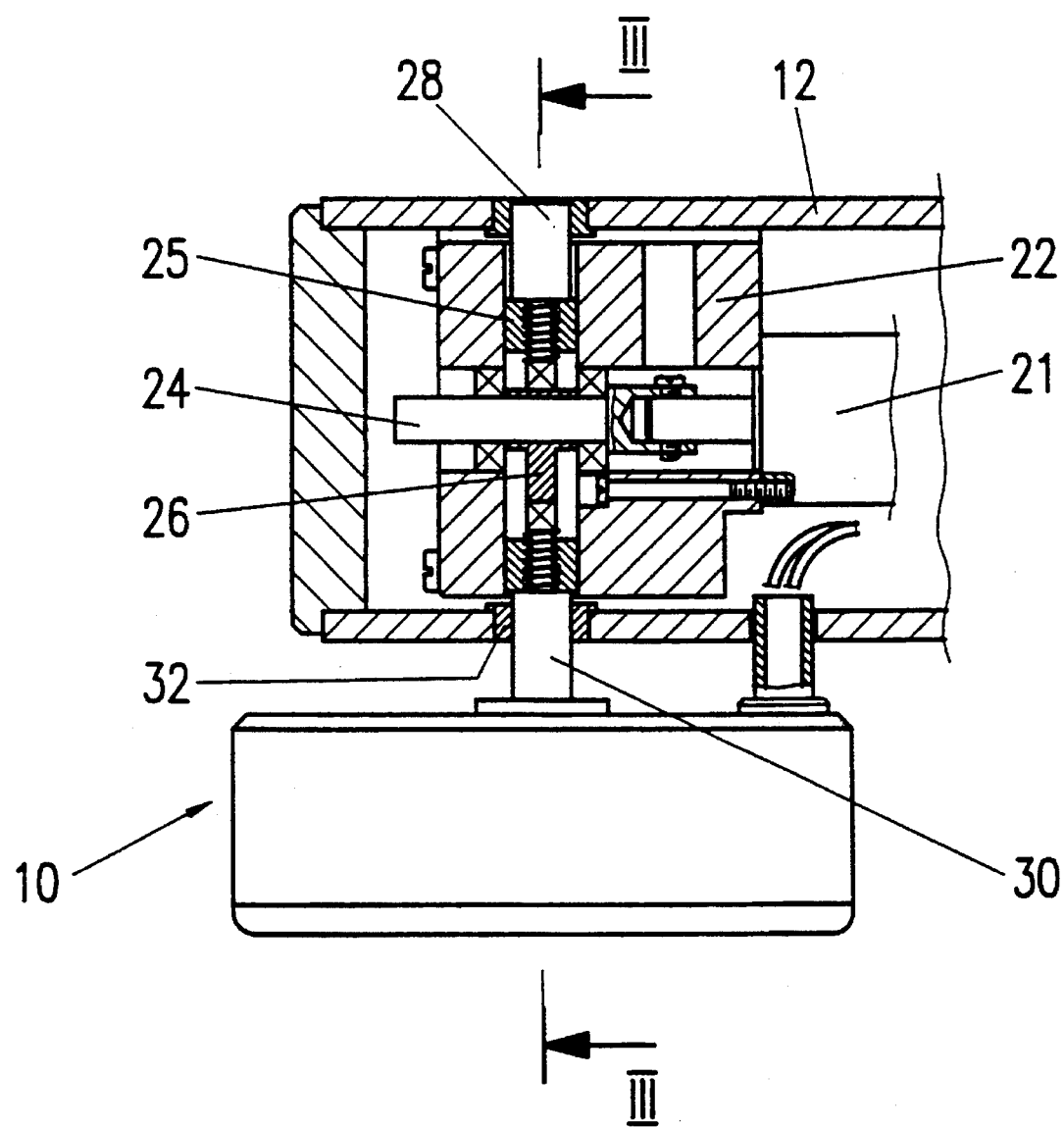
FIG. 2 shows a partly sectioned side view of the pressure element of the apparatus.
Figure 3:
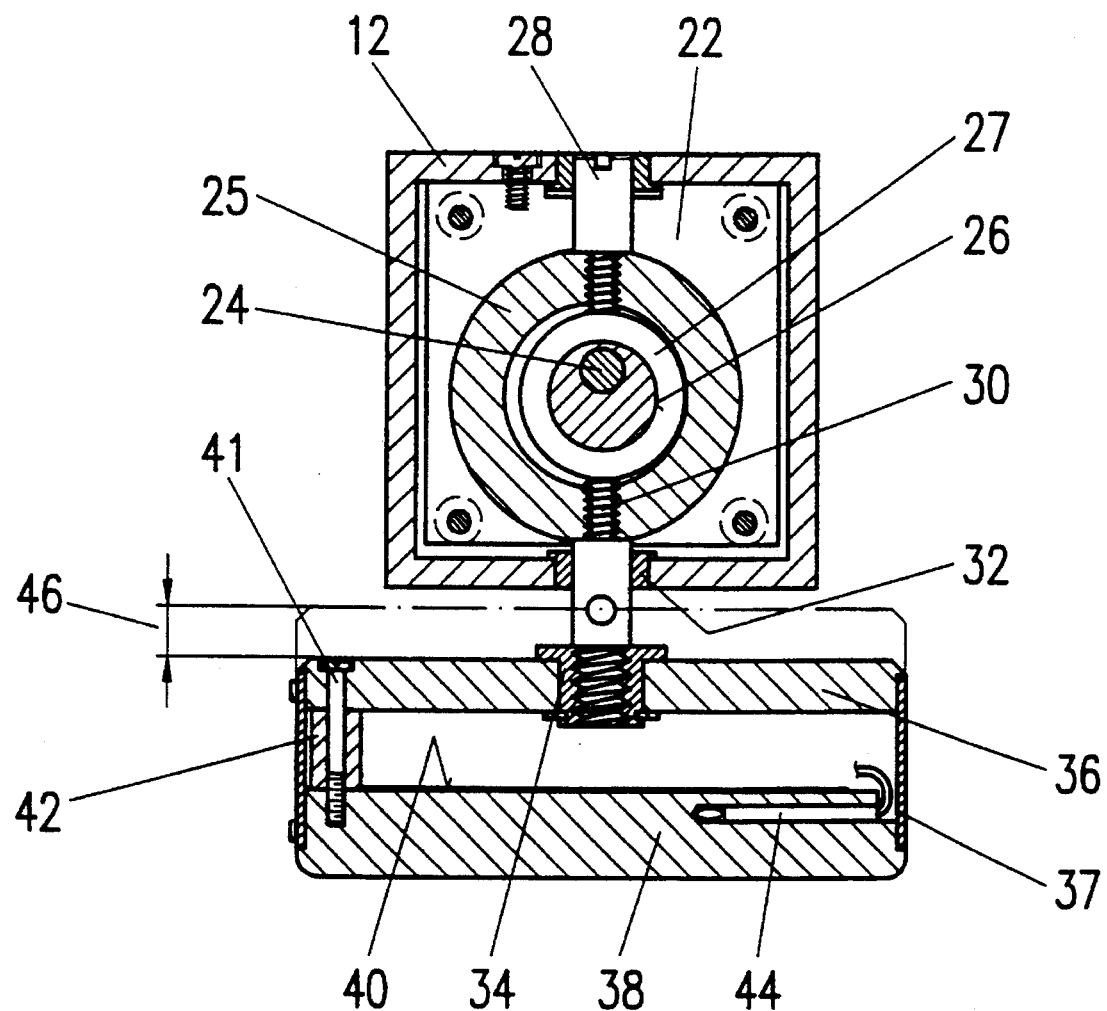
FIG. 3 shows a sectional view in the plane III—III of FIG. 2.

Now, element 10 is to be described together with its additional components. Reference is made particularly to FIGS. 2 and 3.

Near the front end of the upper support bar 12, a gear box 22 is mounted in the interior of the bar 12. An electric motor 20 comprising a reduction gear 21 is flanged to the gear box 22; in the present example, a d.c. minimotor for 12 volts, having a power of 6.8 watts and a speed of 4500 rpm, was used. An eccenter disk 26 which acts upwards through a bearing 27 on a setting screw 28 is solidly fastened on the output shaft 24 of reduction gear 21. The eccenter disk 26 acts downwards through bearing 27 on a pin 30 which is movable in the vertical direction and which extends through a bushing 32 in a bore in support bar 12. A connecting disk is referenced by numeral 25 which circumferentially connects both elements 28 and 30.

At its lower end, pin 30 is connected over a bushing 34 to a circular steel plate 36 which has in the present example a diameter of about 80 to 85 millimeters. A circular pressure plate 38 is bolted with a certain distance to steel plate 36, and FIG. 3 shows one of several screws 41 and spacers 42. The space between steel plate 36 and pressure plate 38 is closed by an annular cover 37. Pressure plate 38 consists of a highly heat conductive metal, e.g. copper or a copper alloy; its lower surface and, optionally, its other outer surfaces are high-polished chromium or nickel plated. The pressure plate 38 can be heated by means of a flat circular heating sheet 40 cemented on the inner surface of the plate; if an aqueous medium is used as an extraction fluid, the plate may be heated to a temperature of, e.g., 90° to 98° C. The heating power of the heating sheet 40 is controlled by means of a temperature probe, for example a Ni-CrNi-thermocouple 44, which is inserted into a horizontal bore of the pressure plate 38, in such a manner that the temperature of the pressure plate is maintained at the desired value. Preferably, the thermocouple acts simultaneously as a temperature controlling and a temperature measuring device, i.e. a thermometer.

The stroke of the eccenter disk 26 is designed in such a manner that the pressure plate 38 exerts a predetermined pressure or force on the substrate, for example about 1000N corresponding, with the surface area to be considered, to a pressure of 1 to 2 bars.

Figure 4:
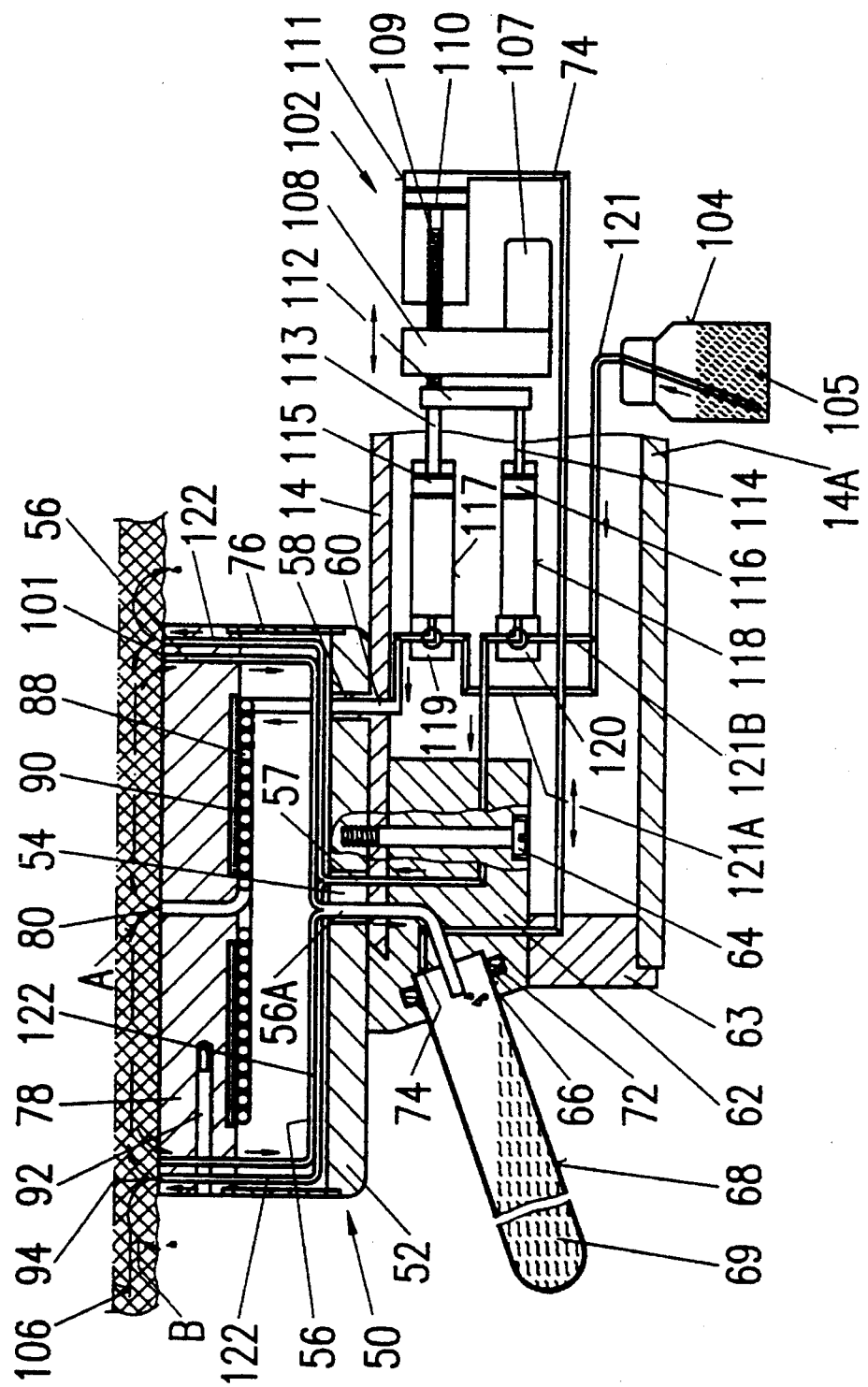
FIG. 4 shows a central vertical sectional view of the collecting element of the apparatus.

FIG. 4 shows a vertical sectional view of the extracting and collecting element 50. It comprises a steel plate 52 having the shape of a circular disk and mounted on the front end of lower support bar 14. The plate has a central bore 54 traversed by two conduits 56A and 57. Furthermore, a lateral bore 58 is provided giving a passage for the extracting fluid supply tube 60.

A lower block 62 is fastened from below to the support bar 14 and the steel plate 52 by means of screws 64. The lower block 62 which is held against the lower rail 14A of the support bar 14 by a supporting and distance block 63 has an angular bore 66 whose longitudinal axis is at an angle of about 20° to the horizontal plane.

A sample tube 68 having a corresponding diameter can be inserted into the bore 66 and is sealed against the wall of the bore by one or more O-rings 72. The main collecting conduit 56 as well as a suction tube 74 open into the sample tube 68.

A lower pressure plate 78 is disposed in a distance from the steel plate 52 above the latter by means of an annular spacer 76 which is inserted into annular grooves of the lower steel plate 52 and the lower pressure plate 78 and fastened to the respective plates by screws (not shown).

The lower pressure plate 78 has substantially the same dimensions as the upper pressure plate 38 of the upper shoe 10. It is also made of superficially chromium or nickel plated and mirror-polished copper in order to ascertain a good heat conductivity and capacity. The lower pressure plate has a central bore 80 which is connected to a flat metal spiral tube 88. This flat spiral 88 contacts and is mounted on the lower, free surface of a flat, circular heating element 90 which corresponds in principle to the upper heating element 40. The permanent contact with the heating element 90 continuously heats the spiral tube 88 to the desired temperature. The lower pressure plate 78 further contains, as in the case of the upper pressure plate 38, a thermocouple 92 for controlling the temperature of the plate 78 as it has already been described with reference to the element 44. The temperature of plate 78 should be the same as that of the upper pressure plate 38. The thermocouple 92 is preferably also a Ni-CrNi element.

A supply tank 104 for extraction fluid 105, for example a bottle, is lodged within the lower support bar 14 (see also FIG. 1). An extracting and collecting mechanism 102 is also located in the lower bar 14. This mechanism comprises an electromotor 107 flanged to a reduction gearbox 108. The output shaft 109 of the reduction gearbox 108 is threaded so that the shaft makes a reciprocating movement when the motor 107 turns in one and in the other sense of rotation. A piston 110 sliding in a cylinder 111 is fastened to the right end (FIG. 4) of the output shaft 109. A bridge or yoke 112 to which two piston rods 113 and 114 are fastened is fixed to the left free end of the output shaft 109; these two piston rods 113, 114 carry pistons 115 and 116, respectively, which slide in cylinders 117 and 118, respectively. The bottom of cylinder 111 is connected by conduit 74 to the sample tube 68. The bottom of each cylinder 117 and 118 is connected to a three-way valve 119 and 120, respectively. The two three-way valves 119, 120 are connected by a conduit 121A, 121B to a combined conduit 121 which leads into the extracting fluid storage vessel 104. The third connection of three-way valve 119 is connected by conduit 60 to metal spiral tube 88. The third connection of three-way valve 120 is connected to a conduit 122 which leads to lower pressure plate 78; its purpose will be described later.

Figure 5:
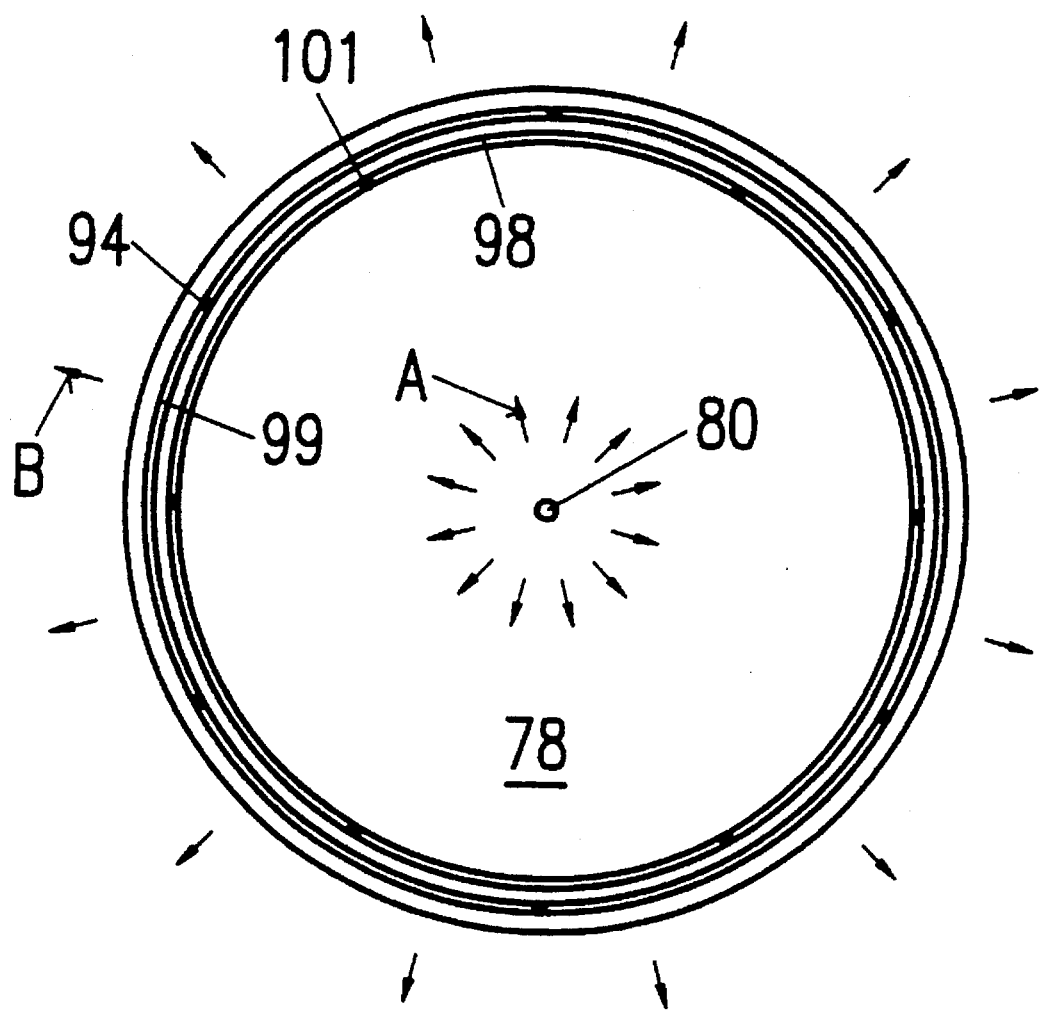
FIG. 5 shows a top view of the collecting element of FIG. 4.

The upper surface of the lower pressure plate 78 comprises means for ejecting extracting fluid and for collecting the extract from the porous material clamped between plates 38 and 78. Reference is now also made to FIG. 5 which shows a top view of lower pressure plate 78. This surface comprises two circular concentrical grooves 98 and 99. Conduits 122 which have already been described above end in barrier groove 99 through several holes 94 which are evenly distributed over the circumference of groove 99. Conduits 56 which merge into the main collecting conduit 56A already described, end in collecting groove 98 through several holes 101 which are evenly distributed over the circumference of groove 98. In the interior of lower shoe 50, i.e. between plates 52 and 78, conduits 56 and 122 are welded or soldered together in order to obtain a heat exchange between the liquids flowing within the conduits.

The method of the invention will now be illustrated in more detail by means of the description how the apparatus which has just been described, will be operated for extracting a textile material, for example a cellulose fiber containing shirt fabric which has received a high-grade reactive resin crease-free finish.

In the rest position, the eccenter disk 26 has been turned such that the upper pressure shoe 10 is in its uppermost position, and a gap of about 7 to 10 mm is free between the upper shoe 10 and the lower shoe 50. The conduits 60 and 122 as well as the cylinders 117 and 118 are in this position already filled with extraction fluid 105 from supply vessel 104, and the three pistons of the extracting device 102 are in the position shown in FIG. 4. The heating elements 40, 90 of the two shoes are energized. When a steady temperature state is reached comprising the desired extraction temperature, for example about 95° C., which requires some minutes only, the fabric 106 is brought between the said shoes 10 and 50. Then, motor 20 is energized which lowers the pressure shoe 10 by means of the eccenter disk 26 until the greatest diameter of the eccenter disk acts upon pin 30 and thus on the pressure shoe 10. In this position, a pressing force of about 1,000 Newton is exerted on the fabric 106. The setting of the adjusting screw 28 and the elasticity of the two supporting bars 12 and 14 together with its connecting traverse 16 is selected such that the said force is stabilized. The free length of the bars 14 and 16 is such that textile materials having current widths can be put between the pressure shoes so that any desired surface region can be analyzed and no region of the textile material remains inaccessible.

Now, motor 107 of the extracting device 102 is energized from the shown position, and shaft 109 is pushed to the left in FIG. 4. The two three-way valves are in the shown position. From cylinder 117 which has an active volume of about 5 ml, exactly 5 ml of extracting fluid are fed into line 60 so that 5 ml of hot extracting fluid, heated within the spiral conduit 88, are ejected through the opening 80 in the plate 78 into the clamped-in textile material 106 and spread in this substrate according to flow arrows A. Simultaneously, about 1.25 ml of barrier fluid, identical to the extracting fluid, are fed from cylinder 118 through conduit 122 and openings 94 into the barrier groove 99 which is situated near the outer edge of plate 78. 1 ml of fluid will circumferentially escape from the clamped-in sample of web 106 according to flow arrows B. The fluids injection is effected during about 20 seconds.

The extraction fluid flows within the clamped-in textile material sample toward the collecting groove 98 which is concentric to the barrier groove 99 and has a radial distance to the latter of some millimeters. During the flow of the extracting fluid, extractable substances within the textile material sample are extracted and carried away with the flowing extracting fluid. The flow of this fluid from the opening 80 to the collecting groove 98 is assisted by an air suction through conduit 56 and conduit 74 which ends in air suction cylinder 111 whose piston 110 is moved from the right to the left during the corresponding movement of the other two pistons 115 and 116, already described above. The extract collects in collecting groove 98 and flows through holes 101 and conduit 56 into the sample tube 68. At the end of the motion of the three pistons 110, 115 and 116, 5 ml of extracting fluid and 1.25 ml of barrier fluid have been fed into the textile material sample, and 5 ml of extract 69 is collected in the sample tube 68. The use of a liquid barrier system ascertains that no extracting fluid can escape from the textile material sample of web 106. The use of a high temperature during extraction ascertains that virtually no solvent will remain in the porous material after extraction.

An important feature of the apparatus and the method of the invention is that the extract collected in conduit 56 is cooled down before reaching the sample tube 68 so that there is substantially no loss of extract liquid by vaporization. In fact, conduit 122 which carries cold fluid from cylinder 118 is thermally connected to conduit 56 in which flows the hot extract to sample tube 68. Thus, the extract is cooled down to about 55° to 65° C. whereas, in a most desired manner, the barrier fluid flowing through conduit 122 is heated to about 80° C.

The two three-way valves 119 and 120 are now turned clockwise by 90°, and the motor 107 is turned on in the inverse sense of rotation. The two pistons 115 and 116 are moved to the right until their end position, and the cylinders 117 and 118 are filled with the measured amount of extracting fluid 105 from supply vessel 104 through conduits 121, 121A and 121B. Finally, the two three-way valves 119 and 120 are rotated counterclockwise by 90° in order to connect the cylinders to conduits 60 and 122, respectively.

The motor 20 is now energized anew and turns the eccenter disk 26 by 180° so that the upper shoe is lifted by about 7 mm, and another region of the material to be analyzed can be clamped in for extraction. Extracting liquid remains within the spiral tube 88, about 5 ml in the present example, which is at the desired temperature so that the next extraction may immediately begin.

The extract 69 collected in tube 68 is ready to be analyzed. To this effect, sample tube 68 is retracted from the apparatus, stoppered and put into an automatic analyzer or any other manual or automatic analyzing device. Such devices are well known to the one skilled in the art and need not be described or shown in the present document. Interesting parameters to be assayed are pH value, color, conductivity, presence and, optionally, amount of certain ions and/or organic substances such as sizing agents, surface tension, viscosity, redox potential, residues and so on.

The apparatus of the invention which has been described generally comprises still other elements, parts and units which are not shown. The process steps described above are preferably run according to an automatic program which may be invariable or adjustable. The steps, operations and actions are preferably displayed. These additional parts and elements are well known to the one skilled in the art and will not be described herein. The apparatus may be diversely modified and adapted to special problems and purposes and conditions of use. For example, it is possible to exchange the pressure and collecting parts, to make the lower shoe vertically displaceable instead of or in addition to the upper shoe. Furthermore, it is not compulsory to dispose the apparatus horizontally as shown; it may be arranged at any angle to the horizontal plane and even vertically (in the case of a vertically extending material web). The two shoes may alternatively be pressed together by pneumatic or hydraulic devices by mounting corresponding driving elements which are known per se.

The present invention provides an apparatus for the execution of a rapid method for the determination of the inner condition of a sheet-like, porous material, in particular of a textile material web, by forced desorption, solution and/or extraction of substances from said material. The sampling requires generally not more than 30 to 60 seconds, and measuring values can be obtained which can immediately be translated into corresponding adaptations of production parameters.

Instead of sheet or web like materials, other materials may sometimes also be analyzed; such materials are for example yarns and filaments which may be put together in parallel rows which will form a bidimensional arrangement that may also be clamped into the apparatus for analysis. Such an analysis may for example determine oversizing of weaving yarns.

The apparatus is a compact and transportable unit which can be approached to any sheet or web like material; therefore, it is no longer necessary to cut pieces or other samples from the sheet and to bring them into a laboratory. It is neither necessary to mount the apparatus into finishing machines or installations in order to obtain extracted samples. It is further possible to equip the apparatus of the invention with a battery powered electric supply which further improves the application possibilities.

The sample tube described above may be replaced by a similar receptacle which is directly connected to an analyzing apparatus or installation; in this case, the analysis may be effected nearly simultaneously with the extraction, and this will provide the analysis data still more rapidly. A process control could directly be influenced by the analysis results.

We claim:

1. An apparatus for the analysis of porous materials which contain extractable substances, in order to determine the inner condition of the material including substances present in or on the material by forced desorption and extraction, wherein the apparatus comprises:

a) a pressure element and a collecting element, both elements having facing contact surfaces and being coaxially arranged and fastened to a support bar system consisting of two parallel support bars having upper and lower surfaces, each of said elements being provided with a heating device;

b) means for pressing said two elements one against the other, said porous material being clamped between said contact surfaces of said elements;

c) means for introducing an extracting fluid through one of said elements into the clamped-in porous material; and d) means for removing an extract formed of said extracting fluid and extracted substances from said material and for collecting the extract.

2. The apparatus of claim 1, wherein said two elements are circular disk-shaped, each element comprising a circular pressure plate equipped with said heating device, each pressure plate being rigidly fastened at an axial distance to a circular mounting plate of a dimensionally stable metal, all said plates having substantially the same diameter.

3. The apparatus of claim 1, further comprising suction means for removing the formed extract from said clamped-in porous material.

4. The apparatus of claim 2, wherein the pressure element is fastened to the lower surface of the first, upper support bar, and the collecting element is fastened to the upper surface of the second, lower support bar.

5. The apparatus of claim 2, wherein the heating devices of the said two pressure plates comprise flat, sheet-like circular heating elements fixed to the inner surface of said pressure plates.

6. The apparatus of claim 5, wherein the said pressure plates further comprise means for measuring and controlling the temperature of said plates.

7. The apparatus of claim 4, wherein the collecting element is rigidly fastened to the said lower support bar, and the pressure element is axially displaceably fastened to the said upper support bar to be pressed against the collecting element.

8. The apparatus of claim 7, wherein the upper support bar contains a driving motor connected to a reduction gearbox having an output driving shaft, an eccenter disk being mounted on said driving shaft, said eccenter disk acting on a pin connected to said pressure element for reciprocating said pressure element to and from said collecting element.

9. The apparatus of claim 2, wherein the outer surface of the pressure plate of said collecting element comprises a central bore for the supply of fresh extracting fluid, a first, circular collecting groove near the outer edge of the pressure plate for collecting the extract, and a second, circular barrier groove disposed between the said first groove and the outer edge of said pressure plate, said two grooves having bores traversing the pressure plate.

10. The apparatus of claim 9, wherein said means for introducing an extracting fluid comprise an extracting fluid storage vessel; a first metering device for supplying metered volumes of extracting fluid to the central bore of said collecting element; a second metering device for supplying metered volumes of extracting fluid to said barrier groove of the pressure plate; a heatable spiral tube for heating extracting fluid supplied by said first metering device; and conduits for connecting said storage vessel to said metering devices and the latter with said spiral tube and said pressure plate.

11. The apparatus of claim 9, wherein said means for removing the said extract comprise several collecting conduits connected to said collecting groove and merging into a main collecting conduit, and a suction device connected by a suction conduit to said sample tube, said main collecting conduit leading into the said sample tube.

12. The apparatus of claim 10, wherein said means for removing the said extract comprise several collecting conduits connected to said collecting groove and merging into a main collecting conduit, and a suction device connected by a suction conduit to said sample tube, said main collecting conduit leading into the said sample tube, and wherein each conduit coming from the second metering device for feeding the extracting fluid to the barrier groove, is in close thermally conductive contact with a collecting conduit coming from the collecting groove.

13. A method for the analysis of a porous material which contains extractable substances, in order to determine the inner condition of the material including substances present in or on the material by forced desorption and extraction, said method comprising the following steps:

a) inserting a porous material between a pressure element and an extracting and collecting element, b) clamping the porous material between said two elements, c) feeding a first metered amount of an extracting fluid into said extracting and collecting element and from that into said porous material, said fluid being heated during its flow towards the extracting and collecting element, and d) collecting an extract from said porous material in a collecting groove near the outer periphery of said extracting and collecting element and directing the extract into a sample receptacle.

14. The method of claim 13, further comprising the step of feeding a second metered amount of extracting fluid as a barrier fluid into a barrier groove near the outer periphery of said extracting and collecting element, simultaneously with the feeding of the first metered amount in step c).

15. The method of claim 14, wherein heat is exchanged between the said barrier fluid and the out-flowing extract.

16. The method of claim 13, further comprising the step of applying a suction to the sample receptacle in order to assist in collecting said extract.

17. The method of claim 13, wherein an aqueous extracting fluid is used.

18. The method of claim 13, wherein the extracting fluid comprises at least in part an organic solvent.

19. The method of claim 13, wherein the extracting fluid contains at least one substance capable of reacting with substances to be extracted in order to improve their extractability.

20. The method of claim 13, wherein the extracting fluid is liquid, and the extracting fluid and the porous material are heated to a temperature slightly below the boiling point of the extracting fluid, namely in the range of from 70° to 100° C.

21. The method of claim 13, wherein the porous material comprises a bidimensional textile material or a dense row of substantially parallel textile fibers.

22. The method of claim 20, wherein the extracting fluid is an aqueous extracting fluid, and the extracting fluid and the porous material are heated to a temperature in the range of from 90° to 95° C.

* * * * *